(12) United States Patent
Rothberg et al.

(10) Patent No.: US 8,512,232 B2
(45) Date of Patent: Aug. 20, 2013

(54) ENDOSCOPIC ILLUMINATION SYSTEM, ASSEMBLY AND METHODS FOR STAGED ILLUMINATION OF DIFFERENT TARGET AREAS

(75) Inventors: Elliott Rothberg, Westborough, MA (US); Doron Adler, Nesher, IL (US); Mark Schnoerr, Bellingham, MA (US); Shai Finkman, Haifa (IL)

(73) Assignee: Gyrus ACMI, Inc., Southborough, MA (US)

( * ) Notice: Subject to any disclaimer, the term of this patent is extended or adjusted under 35 U.S.C. 154(b) by 978 days.

(21) Appl. No.: 12/555,299

(22) Filed: Sep. 8, 2009

(65) Prior Publication Data
US 2011/0060184 A1    Mar. 10, 2011

(51) Int. Cl.
*A61B 1/06* (2006.01)
(52) U.S. Cl.
USPC .................... 600/178; 600/160; 600/172
(58) Field of Classification Search
USPC ............... 600/114, 160, 172, 178, 179, 182
See application file for complete search history.

(56) References Cited

U.S. PATENT DOCUMENTS

| | | |
|---|---|---|
| 3,712,984 A | 1/1973 | Lienhard |
| 4,198,960 A | 4/1980 | Utsugi |
| 4,567,880 A | 2/1986 | Goodman |
| 4,573,450 A | 3/1986 | Arakawa |
| 4,602,281 A | 7/1986 | Nagasaki et al. |
| 4,682,219 A | 7/1987 | Arakawa |
| 4,685,449 A | 8/1987 | Bonnet |
| 4,692,608 A | 9/1987 | Cooper et al. |
| 4,809,680 A | 3/1989 | Yabe |
| 4,832,003 A | 5/1989 | Yabe |
| 4,873,572 A | 10/1989 | Miyazaki et al. |
| 4,884,133 A | 11/1989 | Kanno et al. |
| 4,911,148 A | 3/1990 | Sosnowski et al. |
| 4,925,445 A | 5/1990 | Sakamoto et al. |
| 5,040,068 A | 8/1991 | Parulski et al. |

(Continued)

FOREIGN PATENT DOCUMENTS

| | | |
|---|---|---|
| EP | 0027361 | 4/1981 |
| EP | 0355996 | 2/1990 |

(Continued)

OTHER PUBLICATIONS

Non-Final Office Action dated Jun. 27, 2006 from related U.S. Appl. No. 11/105,808; 7 pages.

(Continued)

*Primary Examiner* — Philip R Smith
*Assistant Examiner* — William Chou
(74) *Attorney, Agent, or Firm* — The Dobrusin Law Firm, P.C.

(57) ABSTRACT

The inventive subject matter is generally directed to an illumination system for staged illumination in an endoscopic procedure. The inventive system generally includes an illumination apparatus supporting a light source that is configured for removable assembly with an endoscope. The assembly is configured for insertion into a natural or artificial passageway in a body. The illumination apparatus has one or more light sources providing a first, relatively high level of illumination suitable for imaging a first, relatively large target area, either alone or in combination with a light source for the endoscope, and after removal of the illumination apparatus from the assembly, the endoscope provides a second relatively lower level of illumination suitable for imaging a relatively small target area.

43 Claims, 5 Drawing Sheets

(56) References Cited

U.S. PATENT DOCUMENTS

| | | | |
|---|---|---|---|
| 5,178,130 A | 1/1993 | Kaiya | |
| 5,187,572 A | 2/1993 | Nakamura et al. | |
| 5,192,286 A | 3/1993 | Phan et al. | |
| 5,251,025 A * | 10/1993 | Cooper et al. | 348/66 |
| 5,301,061 A | 4/1994 | Nakada et al. | |
| 5,307,803 A | 5/1994 | Matsuura et al. | |
| 5,325,847 A | 7/1994 | Matsuno | |
| 5,402,768 A | 4/1995 | Adair | |
| 5,402,769 A | 4/1995 | Tsuji | |
| 5,430,475 A | 7/1995 | Goto et al. | |
| 5,543,831 A | 8/1996 | Tsuji et al. | |
| 5,573,493 A | 11/1996 | Sauer et al. | |
| 5,598,205 A | 1/1997 | Nishioka | |
| 5,607,419 A | 3/1997 | Amplatz et al. | |
| 5,647,840 A | 7/1997 | D'Amelio et al. | |
| 5,704,892 A | 1/1998 | Adair | |
| 5,817,015 A | 10/1998 | Adair | |
| 5,846,183 A | 12/1998 | Chilcoat | |
| 5,850,496 A | 12/1998 | Bellahsene et al. | |
| 5,857,961 A | 1/1999 | Vanden Hoek et al. | |
| 5,863,366 A | 1/1999 | Snow | |
| 5,940,126 A | 8/1999 | Kimura | |
| 5,941,818 A | 8/1999 | Hori et al. | |
| 5,957,834 A | 9/1999 | Mochida | |
| 6,124,883 A | 9/2000 | Suzuki et al. | |
| 6,142,930 A | 11/2000 | Ito et al. | |
| 6,184,923 B1 | 2/2001 | Miyazaki | |
| 6,206,825 B1 | 3/2001 | Tsuyuki | |
| 6,240,231 B1 | 5/2001 | Ferrera et al. | |
| 6,260,994 B1 | 7/2001 | Matsumoto et al. | |
| 6,331,156 B1 | 12/2001 | Haefele et al. | |
| 6,352,531 B1 | 3/2002 | O'Connor et al. | |
| 6,409,658 B1 | 6/2002 | Mitsumori | |
| 6,414,710 B1 | 7/2002 | Takahashi et al. | |
| 6,428,469 B1 | 8/2002 | Iddan et al. | |
| 6,449,006 B1 | 9/2002 | Shipp | |
| 6,459,919 B1 | 10/2002 | Lys et al. | |
| 6,468,204 B2 | 10/2002 | Sendai et al. | |
| 6,471,684 B2 | 10/2002 | Dulak et al. | |
| 6,547,721 B1 | 4/2003 | Higuma et al. | |
| 6,579,224 B1 | 6/2003 | Burton et al. | |
| 6,579,277 B1 | 6/2003 | Rabiner et al. | |
| 6,648,874 B2 | 11/2003 | Parisi et al. | |
| 6,659,940 B2 | 12/2003 | Adler | |
| 6,692,430 B2 | 2/2004 | Adler | |
| 6,702,972 B1 | 3/2004 | Markle | |
| 6,796,939 B1 | 9/2004 | Hirata et al. | |
| 6,831,679 B1 | 12/2004 | Olsson et al. | |
| 6,976,956 B2 | 12/2005 | Takahashi et al. | |
| 6,994,667 B2 | 2/2006 | Singh | |
| 7,030,904 B2 | 4/2006 | Adair et al. | |
| 7,101,379 B2 | 9/2006 | Gregory, Jr et al. | |
| 7,207,980 B2 | 4/2007 | Christian et al. | |
| 7,214,183 B2 | 5/2007 | Miyake | |
| 7,241,262 B2 | 7/2007 | Adler et al. | |
| 7,300,397 B2 | 11/2007 | Adler et al. | |
| 7,413,543 B2 | 8/2008 | Banik et al. | |
| 7,479,106 B2 | 1/2009 | Banik et al. | |
| 7,559,892 B2 | 7/2009 | Adler et al. | |
| 7,591,783 B2 | 9/2009 | Boulais et al. | |
| 7,668,450 B2 | 2/2010 | Todd et al. | |
| 7,938,774 B2 | 5/2011 | Segawa | |
| 7,955,255 B2 | 6/2011 | Boulais et al. | |
| 2001/0026666 A1 | 10/2001 | Ferrera et al. | |
| 2001/0031912 A1 | 10/2001 | Adler | |
| 2001/0040211 A1 | 11/2001 | Nagaoka | |
| 2001/0044571 A1 | 11/2001 | Mitsumori | |
| 2002/0013512 A1 | 1/2002 | Sendai et al. | |
| 2002/0095066 A1 | 7/2002 | Kamrava | |
| 2002/0154215 A1 | 10/2002 | Schechterman et al. | |
| 2002/0177750 A1 | 11/2002 | Pilvisto | |
| 2002/0188175 A1 | 12/2002 | Levine et al. | |
| 2003/0009086 A1 | 1/2003 | Black et al. | |
| 2003/0088254 A1 | 5/2003 | Gregory, Jr. et al. | |
| 2003/0142753 A1 | 7/2003 | Gunday | |
| 2004/0034311 A1 | 2/2004 | Mihalcik | |
| 2004/0039250 A1 | 2/2004 | Tholfsen et al. | |
| 2004/0111012 A1 | 6/2004 | Whitman | |
| 2004/0133075 A1 | 7/2004 | Motoki et al. | |
| 2004/0140425 A1 | 7/2004 | Lizuka et al. | |
| 2004/0193140 A1 | 9/2004 | Griffin et al. | |
| 2004/0230097 A1 | 11/2004 | Stefanchik et al. | |
| 2004/0242962 A1 | 12/2004 | Uchiyama | |
| 2004/0249246 A1 | 12/2004 | Campos | |
| 2005/0075538 A1 * | 4/2005 | Banik et al. | 600/141 |
| 2005/0080342 A1 | 4/2005 | Gilreath et al. | |
| 2005/0096502 A1 | 5/2005 | Khalili | |
| 2005/0119527 A1 | 6/2005 | Banik et al. | |
| 2005/0228361 A1 | 10/2005 | Tremaglio | |
| 2005/0250983 A1 | 11/2005 | Tremaglio et al. | |
| 2005/0267328 A1 | 12/2005 | Blumzvig et al. | |
| 2005/0272975 A1 * | 12/2005 | McWeeney et al. | 600/113 |
| 2005/0277810 A1 | 12/2005 | Irion | |
| 2006/0055793 A1 | 3/2006 | Adler et al. | |
| 2006/0173242 A1 | 8/2006 | Navok et al. | |
| 2006/0183976 A1 | 8/2006 | Adler et al. | |
| 2007/0073107 A1 * | 3/2007 | Peartree et al. | 600/124 |
| 2007/0177009 A1 | 8/2007 | Bayer et al. | |
| 2007/0185386 A1 | 8/2007 | Cheng | |
| 2007/0215268 A1 | 9/2007 | Pingleton et al. | |
| 2007/0270647 A1 * | 11/2007 | Nahen et al. | 600/131 |
| 2007/0276182 A1 | 11/2007 | Adler et al. | |
| 2008/0033423 A1 | 2/2008 | Peacock, III | |
| 2008/0108869 A1 | 5/2008 | Sanders et al. | |
| 2008/0114303 A1 | 5/2008 | Tremaglio | |
| 2008/0183043 A1 | 7/2008 | Spinnler et al. | |
| 2008/0183192 A1 * | 7/2008 | Saal et al. | 606/130 |
| 2008/0221391 A1 * | 9/2008 | Weitzner et al. | 600/118 |
| 2008/0287792 A1 | 11/2008 | St. George et al. | |
| 2009/0036744 A1 | 2/2009 | Vayser | |
| 2012/0143006 A1 * | 6/2012 | Avitsian et al. | 600/121 |

FOREIGN PATENT DOCUMENTS

| | | |
|---|---|---|
| EP | 0647425 A1 | 4/1995 |
| EP | 0573746 | 12/1995 |
| EP | 1202767 | 7/2000 |
| JP | 60104915 | 6/1985 |
| JP | 61281680 | 12/1986 |
| JP | 62-35314 | 3/1987 |
| JP | 63136781 | 6/1988 |
| JP | 63210813 | 9/1988 |
| JP | 04236934 | 8/1992 |
| JP | 05142484 | 6/1993 |
| JP | 06-335450 | 12/1994 |
| JP | 7209590 | 8/1995 |
| JP | 07-275200 | 10/1995 |
| JP | 08024219 | 1/1996 |
| JP | 08050251 | 2/1996 |
| JP | 08114755 | 5/1996 |
| JP | 6366525 | 3/1998 |
| JP | 10151105 | 6/1998 |
| JP | 2000139821 | 5/2000 |
| JP | 2000171727 | 6/2000 |
| JP | 2000206422 | 7/2000 |
| JP | 200234910 | 2/2002 |
| JP | 200258633 | 2/2002 |
| JP | 2002508201 | 3/2002 |
| JP | 2005-525896 | 9/2005 |
| WO | WO9930610 | 6/1999 |
| WO | WO0049448 | 8/2000 |
| WO | WO0162168 | 8/2001 |
| WO | WO0176452 | 10/2001 |
| WO | WO02078632 | 10/2002 |
| WO | WO03013624 | 2/2003 |
| WO | WO03028547 | 4/2003 |
| WO | WO03098913 | 11/2003 |
| WO | WO2005072806 | 8/2005 |
| WO | WO2006032013 | 3/2006 |
| WO | WO2007134341 | 11/2007 |
| WO | WO2007137184 | 11/2007 |

OTHER PUBLICATIONS

Final Office Action dated Dec. 20, 2006 from related U.S. Appl. No. 11/105,808; 7 pages.

Decision on Appeal dated Jun. 25, 2010 from related U.S. Appl. No. 11/105,808; 8 pages.

U.S. Patent and Trademark Office Action dated May 22, 2009 for related U.S. Appl. No. 11/109,041, filed Apr. 18, 2005; 21 pages.

Applicant's response to U.S. Patent and Trademark Office Action dated May 22, 2009 for related U.S. Appl. No. 11/109,041. Response filed Aug. 19, 2009; 18 pages.

Japanese Office Action dated May 19, 2011, for Japanese Patent Application No. 2010-278712 (in Japanese language); 6 pages total. (English translation included).

Office Action dated Jun. 17, 2011 from the Patent Office of Japan in Japanese Patent Application No. 2004-506277; 5 pages. English translation included.

Examination Report from the German Patent and Trademark Office dated Jul. 12, 2010 for related German patent application No. 102008018931.6; informal English translation provided by German agent is included; 10 pages total.

Office Action dated Sep. 2, 2011 from the United States Patent and Trademark Office for U.S. Appl. No. 12/104,382: 12 pages.

PCT International Search Report and Written Opinion dated Sep. 27, 2010 for related patent application No. PCT/US2010/040100, filed Jun. 25, 2010; 13 pages.

United States Patent and Trademark Office Final Office Action dated Nov. 9, 2010 for related U.S. Appl. No. 11/109,041, filed Apr. 18, 2005; 13 pages.

Office Action dated Dec. 13, 2011 from the Patent Office of Germany in German Patent Application No. 10392670.4; 9 pages.

Japanese Office Action dated Mar. 18, 2009, for corresponding Japanese patent application No. 2004-506277; English translation included; 4 pages.

Japanese Office Action dated Dec. 22, 2009, for a related Japanese Patent Application No. 2004-506277; 11 pages. English translation included.

Final Office Action dated May 28, 2010 from related U.S. Appl. No. 10/514,607; 12 pages.

Non-Final Office Action dated Jul. 22, 2009 from related U.S. Appl. No. 10/514,607; 11 pages.

Non-Final Office Action dated Nov. 24, 2009 from related U.S. Appl. No. 10/514,607; 10 pages.

Japanese Office Action dated Jan. 25, 2011, for a related Japanese Patent Application No. 2004-506277; 9 pages. English translation included.

Japanese Office Action dated Aug. 17, 2010, for a related Japanese Patent Application No. 2004-506277; 6 pages. English translation included.

* cited by examiner

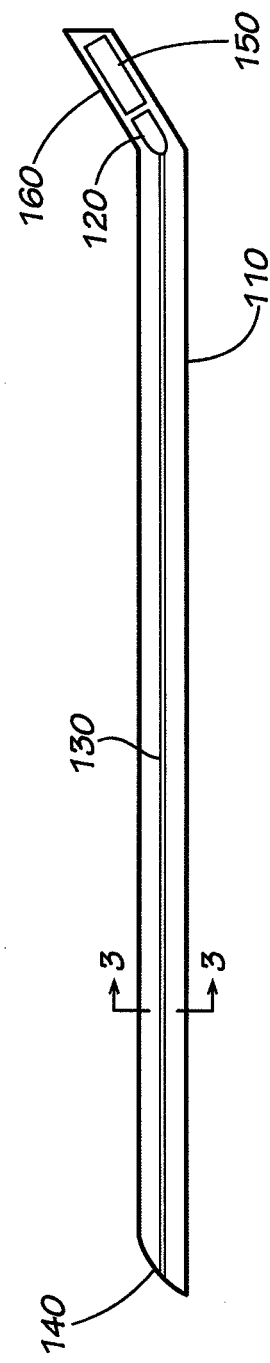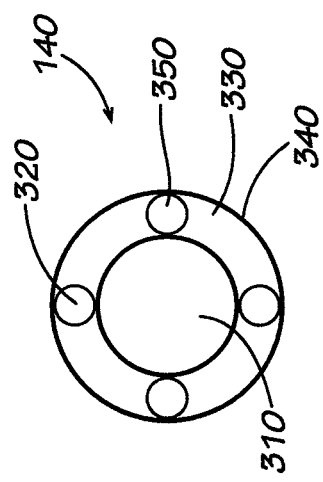

ENDOSCOPIC ILLUMINATION SYSTEM, ASSEMBLY AND METHODS FOR STAGED ILLUMINATION OF DIFFERENT TARGET AREAS

BACKGROUND

The inventive subject matter described herein is generally related to the field of medical endoscopy and in particular to illumination systems for endoscopes.

In minimally invasive surgery and medical procedures, endoscopes are intracorporeally placed into natural or artificial passages, channels, and cavities of a patient, which may be a human or an animal. The more narrow an intended passageway or target site, the smaller the imaging system and illumination system must be to avoid trauma and invasiveness from the endoscopic system. Therefore, endoscopy systems generally have miniaturized imaging and illumination systems to allow for insertion to a target site. Because of the tiny size of the imaging systems and the insufficiency of light in the target site, illumination systems must be associated with imaging systems so that sufficient light is delivered to a target site.

Unfortunately, illumination systems that are effective at illuminating a small target site may not provide sufficiently bright or dispersed light for a larger target area. Therefore, in some procedures where there is a need to inspect or view variably-sized target sites, different endoscopic system must be used to provide target-specific illumination levels. This is problematic because using extra equipment means extra steps, extra risk of infection and trauma, extra costs, and extra burden on operating room spaces and resources.

One case that illustrates the foregoing problems is related to ureteroscopic procedures. A ureteroscope is relatively small so that it can get into tiny places, such as the small cavity of the ureter. The ureteroscope carries its own illumination source on its insertion end that is capable of illuminating the small cavity of the ureter and the renal pelvis. However, because of the small size of the ureteroscope, its illumination system does not sufficiently illuminate the larger bladder cavity, which it must negotiate on its way to the ureter. Therefore, currently, physicians performing a ureteroscopic exam or procedure must first use a relatively larger endoscope, called a cystoscope, to examine the bladder and access the ureteral orifice for placement of a guidewire. A cystoscope is used instead of the ureteroscope because it outputs relatively high illumination levels specific to visualize the relatively large bladder cavity. Once the guidewire has been placed, the cystoscope is removed. A ureteroscope is then placed on the guidewire, passed along the guidewire past the ureteral orifice, and used for the remainder of the procedure. The problem with this method is that the cystoscope and all of the attendant equipment required (light cable, different control box, other accessories) are used for a brief time during the procedure and then must take up a significant amount of space on the equipment table behind the physician. This also requires additional sterilization cycles for the cystoscopic equipment, even though it is only used for a short time.

Accordingly there is a need for improved endoscopic illumination systems that overcome the prior art by providing for staged illumination of different target areas having different illumination needs in an endoscopic procedure. There is also a need for more efficient systems that eliminate the extra equipment, steps, resources, risks, and costs associated with multiple endoscopic systems being used in a single medical or surgical procedure, such as the cystoscopic inspection that is now associated with a ureteroscopic procedure.

SUMMARY

The inventive subject matter overcomes the disadvantages in the prior art by providing illumination systems, assemblies, and methods for staged illumination in an endoscopic procedure of different target areas having different illumination needs and which may also have different size constraints. The inventive subject matter requires use of only a single endoscope and is thereby eliminates the inefficiencies in the prior art. In certain embodiments, the inventive subject matter provides a replacement for the cystoscope that allows the physician to use the ureteroscope for inspecting both the bladder and ureter/renal areas.

To refer to parts of the illumination system, the following convention will be adopted. The direction towards the endoscope handle, conventionally known as the proximal end, will be referenced as the "handle end" for simplicity whether referring to the endoscope, or a part fitting over the endoscope or within the working channel of the endoscope. The direction towards the insertion into the body, known conventionally as the distal end, will be referenced as the "insertion end" for simplicity whether referring to the endoscope, or a part fitting over the endoscope or within the working channel of the endoscope.

The inventive subject matter is generally directed to an illumination system for staged illumination in an endoscopic procedure. The inventive system generally includes an illumination apparatus supporting a light source that is configured for removable assembly with an endoscope. The assembly is configured for insertion into a natural or artificial passageway in a body, and the illumination apparatus and endoscope are arranged so as to allow the illumination system to illuminate a target site and for an imaging system for the endoscope to receive the reflected light. The illumination apparatus has one or more light sources providing a first, relatively high level of illumination suitable for imaging a first, relatively large target area, either alone or in combination with a light source for the endoscope, and after removal of the illumination apparatus from the assembly, the endoscope provides a second relatively lower level of illumination suitable for imaging a relatively small target area.

In the foregoing embodiment, the illumination apparatus may further include an opening near the handle end to fit the endoscope and hold the handle end of the illumination apparatus fixedly relative to the endoscope. The endoscope may further include a Luer-type fitting and the opening to fit the endoscope may fit by surrounding the Luer-type fitting. The opening may include a breakable tab that breaches the opening when the breakable tab is broken.

In one possible embodiment in which the endoscope is a ureteroscope, the light source is supported on the insertion end of an access sheath. The endoscope is placed in the access sheath and the assembly is inserted in the passageway leading to the target area. This assembly enables additional light to be provided from the sheath's larger diameter, which makes the entire field of vision in the target area brighter and clearer. In addition, the semi-rigid structure of the sheath facilitates access to the ureteral orifice for the placement of the guidewire.

In one possible embodiment, a method of staged illumination in an endoscopic procedure comprises: introducing an endoscope comprising an endoscope light source and an illumination apparatus comprising an illumination apparatus light source into a body through a passageway; illuminating a target site within the body using both the endoscope light source and the illumination apparatus light source; wherein the endoscope light source alone would not have been sufficient to illuminate the target site; and wherein a second endoscope is not used.

These and other embodiments are described in more detail in the following detailed descriptions and the figures.

The foregoing is not intended to be an exhaustive list of embodiments and features of the inventive subject matter. Persons skilled in the art are capable of appreciating other embodiments and features from the following detailed description in conjunction with the drawings.

BRIEF DESCRIPTION OF THE DRAWINGS

The following figures show embodiments according to the inventive subject matter, unless noted as showing prior art.

FIG. 1 is a schematic view of one possible embodiment of an illumination apparatus having a light source for use with an endoscope.

FIG. 2 is a schematic view of one possible embodiment of an endoscope for use with the illumination apparatus of FIG. 1.

FIG. 3 is a distal end view of the illumination apparatus of FIG. 1.

DETAILED DESCRIPTION

Figure 4:
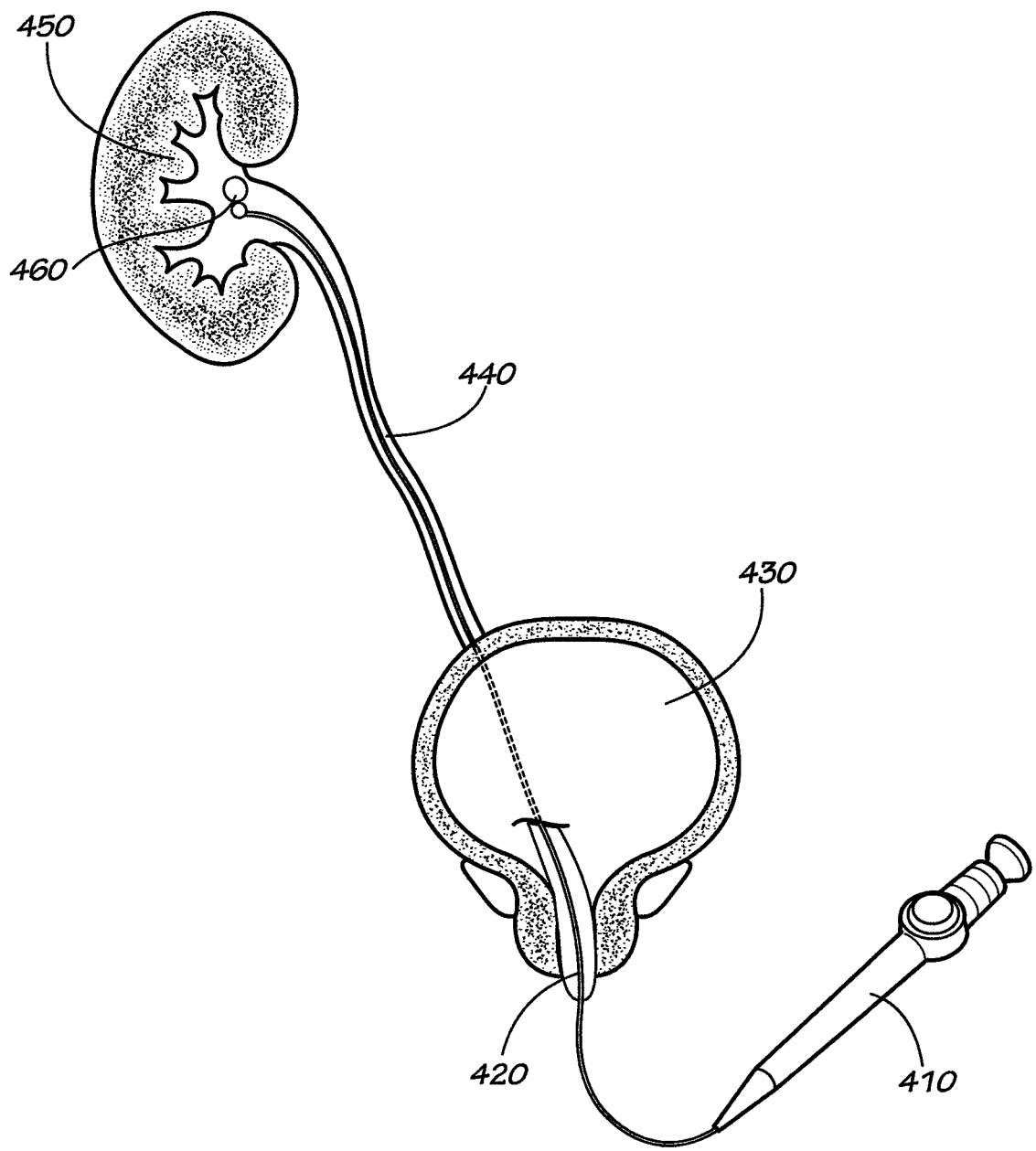
FIG. 4 illustrates one possible environment for use of the inventive subject matter, namely a bladder, kidneys and interconnecting ureter, with a flexible ureteroscope placed through the anatomical areas.

Representative embodiments according to the inventive subject matter are shown in FIGS. 1-8, wherein the same or generally similar features share common reference numerals. The inventive subject matter is generally directed to illumination systems, assemblies, and methods of use and manufacture for staged illumination in an endoscopic procedure of different target areas having different illumination needs and which may have different size constraints.

As used herein, "light emission device" means a source of emission that directly or indirectly emits light in a wavelength usable with an image sensor such as a conventional CCD or CMOS sensor used in medical, endoscopic imaging, including visible, infrared, and/or ultraviolet frequencies. Some examples of possible light emission devices are LEDs, OLEDs, and laser diodes. The light emission device may provide continuous or pulsed emission. As used herein, "light source" means the output window on the insertion end of an apparatus or instrument inserted in to a body. For example, one or more light emission devices can be located at the handle end of an illumination apparatus and arranged as a light source at the insertion end. As another example, the light emission devices may be located at the insertion end and serve as light sources at the insertion end. As yet another example, the light emission devices may be located on the endoscope and provide light to light sources at the insertion end of the illumination apparatus. As used herein, a "light carrier" communicates light from the light emission device to the light source, for example, an optical fiber or guide. Transmission losses along the light carrier may be relatively low, such as 1% loss. Alternatively, the light carrier may have transmission losses of 25%, 50%, or 75%, but a stronger light emission device may compensate. It may be helpful to use a material with higher transmission losses in exchange for other advantages such as flexibility, sterilizability, durability, single-mold constructability, or other advantages.

Representative imaging technology usable in the inventive subject matter is disclosed in U.S. Pat. No. 6,659,940, entitled "IMAGE SENSOR AND AN ENDOSCOPE USING THE SAME".

FIG. 1 depicts one possible embodiment of the inventive subject matter. This embodiment comprises an illumination apparatus 110 having an insertion end 140 and a handle end 160. The illumination apparatus 110 is configured for removable assembly with an endoscope. The handle end 160 includes one or more light emission devices 120. Other embodiments may include any number of light emission devices including one, two, three, four, five, six, seven, eight, nine, ten, or more. Four light conduits 130 transport light from the light emission devices 120. This embodiment has one light conduit for every light emission device. However, other embodiments may use a plurality of conduits per light emission device. Alternatively, each conduit may be supplied by a plurality of light emission devices. The light conduits run from the light emission devices 120 to the insertion end 140, forming four light sources (not shown). This embodiment incorporates an on-board power source 150. This power source may be a battery, capacitor, inductive power receiver, or may be a direct current rectifier and/or transformer for supplied alternating current power.

FIG. 2 depicts one possible embodiment of an endoscope 210. The illumination apparatus may be slideably associated with the endoscope or otherwise removably associated with it. For example, it may be removably coupled using close-fitting, frictional engagement, clips, snaps, male-female parts, etc.

FIG. 3 shows a transverse slice through the insertion end 140 of the illumination apparatus. The illumination apparatus comprises an outside surface 340 and a channel 310 for slideably receiving an endoscope with a guidewire. In this embodiment, for example, the outside surface 340 may have an outer diameter of 16-20 Fr in the French Gauge system, although larger or smaller diameters are contemplated. In this embodiment, for example, the outer diameter of the channel 310 may be 12 Fr, although larger and smaller diameters are contemplated. Four light conduits 320 are evenly spaced around the periphery of the illumination apparatus body 330. The illumination apparatus body may completely surround the light conduits, separating them from contact with the air in the channel 310 or the outer surface 340. Other embodiments may include light conduits that contact the outer surface 340 and/or the channel 310. For instance, US Publ. No. 2007/0185386 to Cheng discloses light emission devices disposed on the outer surface of an endoscope tube. The light emission devices are selected from special, thin LED-type light sources that can be applied to the outer surface of the endoscope to minimize outer diameter. These devices could be adapted for application to an illumination apparatus or endoscope, as described herein.

Numerous materials are contemplated for constructing the light conduits. One possible material is poly(methyl methacrylate) or PMMA. Silica glass may be used. Silica glass may be doped with materials to raise the refractive index such as germanium dioxide or aluminum oxide or to lower the refractive index such as fluorine or boron trioxide. Other materials suitable for manufacturing optical fibers such as fluoride glass or phosphate glass may be used.

The light conduits 320 may optionally include a cladding 350 on the outside. This cladding may be composed of the same materials as the light conduits with a lower index of refraction. Alternatively, an entirely different material may be used.

The illumination apparatus body may be composed of the same materials as the light conduits, the same materials as the cladding (if present), or different materials. The illumination apparatus body may be composed of polytetrafluoroethylene (PTFE), nylon, polyoxymethylene (POM), or any other materials typically used for construction of a urethral access sheath, or any other suitable materials. The illumination apparatus body may optionally include an outer and/or inner cladding made of a different material with better biocompatibility.

The illumination apparatus body may be constructed as a single molded piece, whether or not it is composed of similar or dissimilar materials.

The light conduits may be shaped with a round cross section. Alternatively, other shapes such as a square cross section or a radial section of the illumination apparatus body may be used.

In certain embodiments, the illumination apparatus consists of an elongated element that is slideably associated with the endoscope or otherwise removably associated with it. For example, the elongated element can be an apparatus whose sole purpose is to support a light source. Or it may be a device that performs other functions in a medical procedure. For example, as discussed in more detail below, the elongated element may be a bladder access sheath, a ureteral access sheath, a guide wire, a catheter, or a stent supporting a light source.

The illumination assembly is configured for insertion into a natural or artificial passageway in a body, and the illumination apparatus and endoscope are arranged so as to allow the illumination apparatus to illuminate a target site via light sources and for an imaging system to receive the reflected light. This imaging system may be an image sensor located in the endoscope or the endoscope may include an optical train to an off-board image sensor located outside the endoscope. The illumination apparatus has a light source providing a first, relatively high level of illumination suitable for imaging a first, relatively large target area, either alone or in combination with a separate light source of the endoscope. After removal of the illumination apparatus from the assembly, the endoscope provides a second relatively lower level of illumination suitable for imaging a relatively small target area.

The inventive subject matter is particularly intended for use in minimally invasive surgical or medical procedures where outer diameter of instruments (or other corresponding dimensionality measurement for objects having non-circular cross-sections) needs to be minimized. To minimize invasiveness, the inventive subject matter supports a light source on a separate apparatus so that the endoscope's light source is either supplemented or substituted, thereby providing more illumination than the normal illumination system of the endoscope. Particular advantages can be achieved by supporting the light source on an instrument that is normally used with an endoscope in a particular procedure so that additional instruments and steps are not required in the procedure.

The illumination apparatus can either be something through which the endoscope is removably enclosed for insertion into the passageway. Or it can be something that is enclosed by the endoscope and co-inserted, e.g., a working channel in the endoscope.

In one possible embodiment, the light source is supported on the insertion end of an access sheath sized and shape for passage into a first target area that is relatively large. The access sheath may be rigid or semi-rigid. A semi-rigid access sheath would have at least enough rigidity to be pushed into the first target area. The design of such a sheath is well within the knowledge and skill of persons skilled in the art. An endoscope is placed in the access sheath, and the assembly is inserted into the first target area. This assembly enables additional light to be provided from a light source supported on the sheath's larger diameter, which makes the entire field of vision in the first target area brighter and clearer. In addition, a semi-rigid structure of the sheath may help facilitate access to a second target area that is relatively smaller than the first target area, or to an orifice or passageway leading to the second target area from the first target area, for placement of a guidewire or the endoscope, if a guidewire is not used.

The inventive subject matter contemplates various ways of delivering light via a sheath or other that is removably assembled to an endoscope to provide a first, relatively high level of illumination of a first target area either alone or in combination with the illumination system onboard the endoscope. Hereinafter, an access sheath may be used in illustration of a representative elongated element supporting an illumination system.

In one possible embodiment, the light is delivered to the sheath using self-contained LEDs or other solid-state light emission devices, such as OLEDs, in the disposable sheath directly at the tip. Hereinafter, LEDs will be discussed as representative light emission devices, but other known or to be discovered light emission devices may also be used if they meet requirements for on-board medical endoscope use, such as small size, relatively low power and low heat output, durability, etc.

Figure 5:
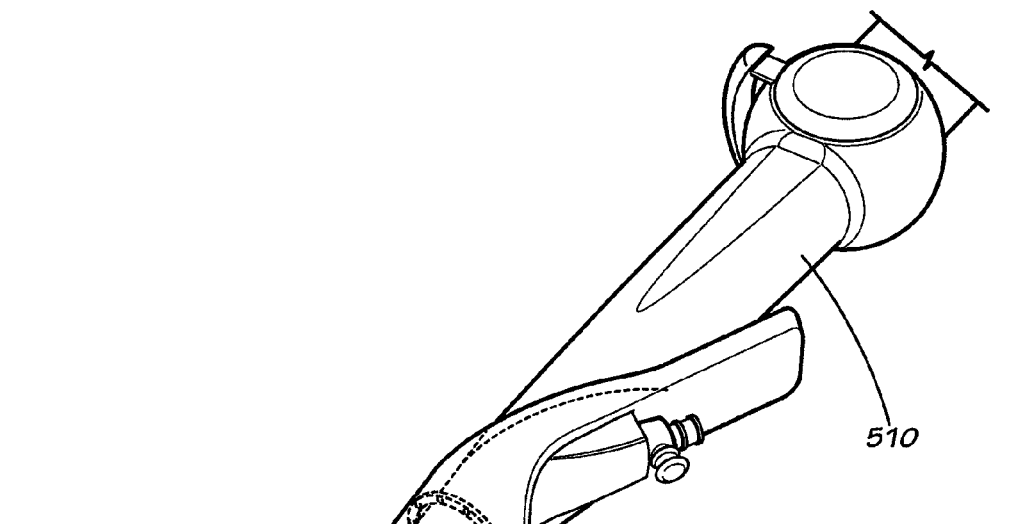
FIG. 5 is a cutaway perspective view of an assembly of an access sheath and an endoscope according to one possible embodiment.

FIG. 5 shows another possible embodiment. The illumination apparatus 510 includes a plurality of embedded light emission devices, shown here as ten LEDs 520 arranged in a circle. Some parts shown in FIG. 6 were removed from FIG. 5 to better illustrate LEDs 520.

Figure 6:
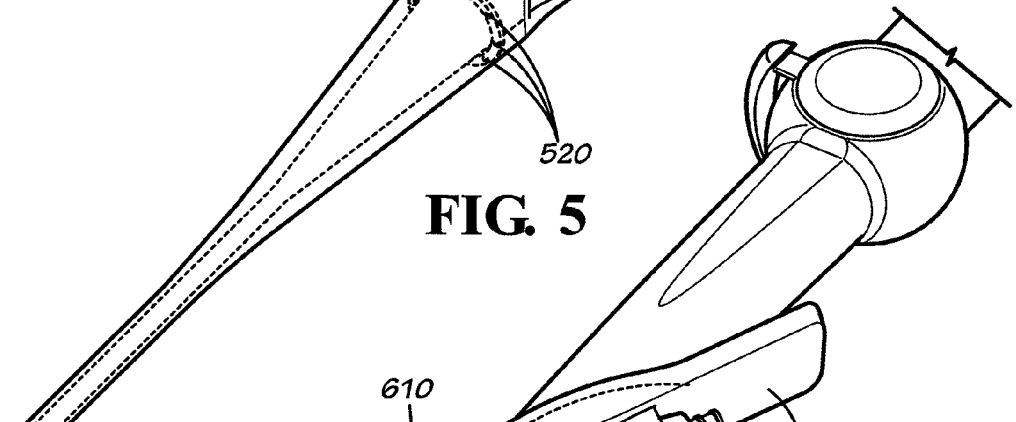
FIG. 6 is a cutaway perspective view of the same assembly of an access sheath and an endoscope according to the embodiment shown in FIG. 5.

FIG. 6 shows a plurality of light carriers 610, shown here as ten. Each light carrier 610 connects directly to one of the LEDs. Thus, this embodiment features a single carrier for a single light emission device.

The illumination apparatus may be designed with an opening to fit around the endoscope handle and prevent the illumination apparatus from moving or becoming dislodged. One feature suitable for such wraparound engagement, if present, is a Luer-type connector. An optional breakable tab 620 may also be included, such that when the tab is removed, the opening is breached. In the case of a Luer-type connector, the illumination apparatus no longer surrounds the Luer-type connector of the endoscope. When the breakable tab 620 is broken, the illumination apparatus may be removed without withdrawing the endoscope. In addition, the breakable tab may provide a convenient location for the power source, such as batteries or capacitors. In the case where batteries contain toxic components such as mercury or cadmium or present a possible explosive risk in the case of lithium batteries, there are significant advantages in facilitating separate disposal of the power source versus the rest of the illumination apparatus. Alternatively, the breakable tab may be reusable and rechargeable, while the rest of the illumination apparatus is disposable. In the foregoing embodiment, the breakable tab may be a power connector from a non-disposable power supply wherein the power connector forms the opening rather than the breakable tab.

Figure 7:
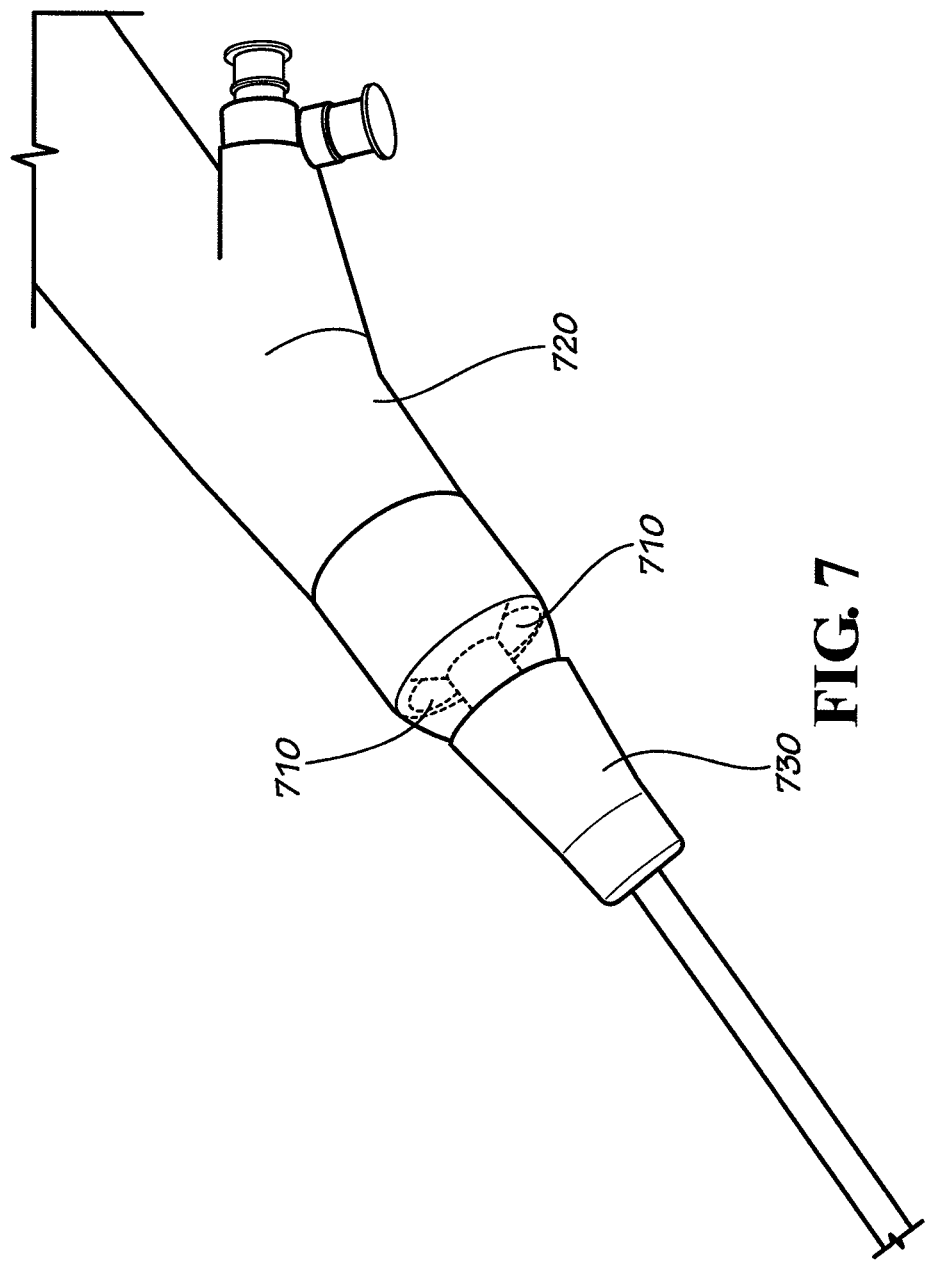
FIG. 7 shows an example light source cone that is installed on an endoscope, which in this case is a flexible ureteroscope.

FIG. 7 shows another possible embodiment. The endoscope 720 includes a plurality of four LEDs 710 mounted on the scope handle.

Figure 8:
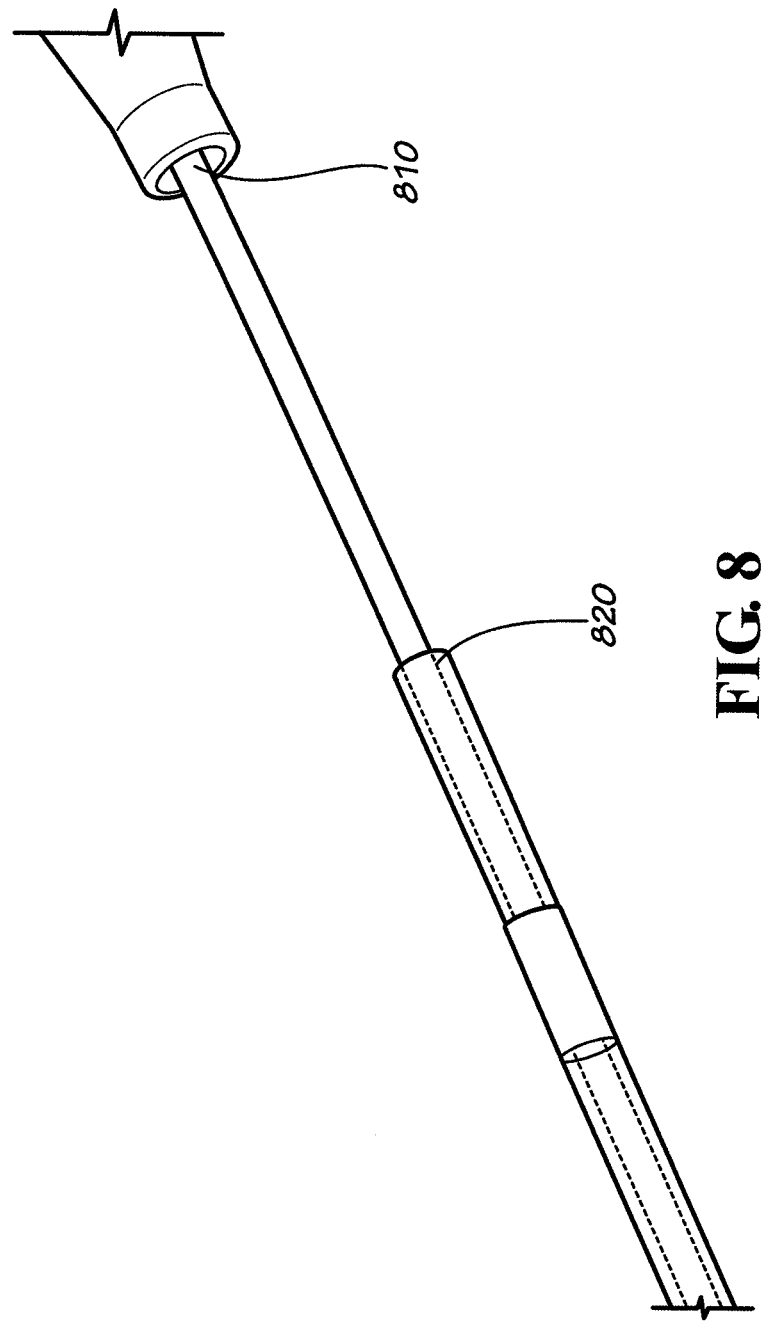
FIG. 8 shows an illumination apparatus, in this case a bladder access sheath, being installed on a proximal portion of the endoscope of FIG. 7.

FIG. 8 shows the same embodiment and illustrates a light source 810 where the light from the four LEDs is emitted. A reflective chamber 730 conveys the light internally from the LEDs to the handle end of the illumination apparatus. Disposable sheath 820 is shown comprising a single light carrier around its entire circumference and length. Light from all four LEDs is transmitted along this single carrier to a light source at the insertion end of the illumination apparatus 820.

In another possible embodiment, a channel in the endoscope is used to support an illumination apparatus with a light source. The illumination apparatus could be a light carrier that is coupled to a light source on the non-insertion portion of the endoscope. The light source could be mated with and optically coupled to a light emission device at the handle end of the endoscope, on the sheath, or elsewhere. Or it could be one or more LEDs that are inserted into the channel and extend off a filament or arrangement of filaments that extend from a proximal portion of the endoscope so that the light source may be removably inserted into the channel. For example, if the sheath is considered optional, a flexible light source could be introduced down the inner diameter of the working channel of the ureteroscope. There would need to be sufficient space reserved in the working channel for the guidewire to still be introduced in this version. US Publ. No. 2005/0250983 to Tremaglio et al., which is under common ownership with the inventive subject matter described herein, discloses an endoscopic device having a filamentous shaft supporting an image sensor and a light source. The teachings of this patent document relative to the construction of a filamentous shaft and light source may be used in view of the inventive subject matter described herein to provide an illumination apparatus usable within the channel of an endoscope.

The light source or sources supported on the illumination apparatus and/or endoscope may be oriented to emit light in the direction of the longitudinal axis of the instrument and/or at any transverse angle so that target areas can be illuminated at most any direction relative to the front or sides of the insertion end of the light source. Imaging systems on an endoscope may be similarly oriented for imaging.

The inventive subject matter contemplates various ways of powering an on-board light emission device for delivering light via a sheath or other illumination apparatus that is slideably, removably assembled to an endoscope to provide a first, relatively high level of illumination of a first target area either alone or in combination with the illumination system onboard the endoscope.

In one possible embodiment, the light emission device is powered using batteries, capacitors, inductive power receiver, direct current rectifier and/or transformer for supplied alternating current power, or another known or to be discovered energizing device. In another possible embodiment, the light emission device is powered using a small cable or other conductor that connects to external power source.

FIG. 4 shows one possible application of the inventive subject matter related to ureteroscopy. This procedure involves piloting a ureteroscope 410 through the urethra 420 into the bladder 430 and up the ureter 440 to the kidney 450. However, the ureter can be difficult to locate without considerable illumination. Typically a cystoscope is first introduced which provides sufficient light to locate the ureter. The cystoscope is then withdrawn and a ureteroscope 410 is introduced. However, the inventive subject matter may be applied to supply additional light from a urethral access sheath, removing the need for a cystoscope. In this context, some embodiments according to the inventive subject matter provide a replacement for the cystoscope that allows the physician to use the ureteroscope for both functions, namely inspection of the bladder and ureter/renal areas. In one possible embodiment, presented for illustration purposes only and not intended to limit the scope of invention, the inventive subject matter could be configured and implemented as follows:

An illumination apparatus in the nature of a sterile, single use, disposable, bladder access sheath that contains light fibers that transmit high-output LED light The disposable sheath would be used in conjunction with a flexible ureteroscope to initially visualize the bladder and access the ureteral orifice. This combination of instruments could be used instead of a cystoscope, which is commonly used at the beginning of a ureteroscopy to achieve this same purpose.

For the ureterscopic procedure, a suitable disposable sheath could have a length of about 20 cm; an outer diameter of about 16 to about 20 Fr; and inner diameter of about 12 Fr (assuming a 10 Fr outer diameter of ureteroscope, which would allow for fluid flow to come back out through sheath during procedure).

The sheath may be fairly stiff to assist in navigating to the ureteral orifice.

The sheath may be tapered at tip to be atraumatic.

The sheath may be hydrophilic coated for ease of insertion.

The light emission devices for the light source for the sheath may be battery powered so as to eliminate cables. Batteries would last length of procedure and then product is discarded. Multiple LEDs and batteries could be used to provide sufficient illumination for the procedure.

The proximal end portion of sheath may be funnel shaped to assist in easy insertion of ureteroscope. The exterior profile need not follow the funnel shape if more space is required for LEDs and battery.

Variations could be:

How the illumination apparatus is associated with a bladder access or other kind of sheath:
  self-contained LEDs directly at the insertion end tip or
  self-contained LEDs in the proximal (handle) end of the sheath with some means (such as light carriers) conveying the light to the distal tip or
  possibly LEDs mounted on the exterior circumference of the ureteroscope handle that a disposable sheath mates to and then transmits the light to the distal tip of the sheath Power for the illumination apparatus may be:
  self-contained with batteries or
  small cable that connects to external power source The geometry of the additional illumination apparatus contained in the sheath as described above or
  if the sheath is considered optional, the flexible light source could be introduced down the inner diameter of, for example, the working channel of the ureteroscope. There should be sufficient space reserved for the guidewire still to be introduced in this version, unless a separate channel can be used.

How the sheath is disposed of at the end of its use
  by removing the ureteroscope sheath combination and then taking the sheath off before reintroducing the ureteroscope or
  by designing the sheath to have a weak 'tear strip' or similar feature such that the sheath can be 'ripped off at the end of its use without having to completely withdraw the ureteroscope.

A typical scheme for use, which again is not intended to be limiting, could be used is as follows:

Preload the sheath onto the ureteroscope.

Insert the ureteroscope first by itself to visualize the urethra.

Once the ureteroscope is at the bladder neck, activate the light in the sheath and advance forward through the urethra to light the bladder for ureteroscopic bladder examination and/or treatment.

Advance the combination of sheath and ureteroscope to access the ureteral orifice.

The ureteroscope can flex the final amount to advance the guidewire into the ureteral orifice and up the ureter.

The bladder may be drained/filled by using a 4×4 gauze square around the scope/sheath interface area.

The physician would then remove the scope and bladder access sheath, leaving the guidewire in place.

The bladder access sheath would be removed from the ureteroscope and then the ureteroscope would be reinserted over the guidewire and advanced up the ureter to treat a stone or perform any other ureteroscopic procedure.

The inventive subject matter contemplates various ways of removing a sheath, particularly a disposable sheath that is slideably, removably assembled to an endoscope to provide an assembly having first, relatively high level of illumination of a first, relatively large target area either alone or in combination with the illumination system onboard the endoscope, and a second, relatively low level of illumination for a relative small target area after removal of the sheath.

After the access sheath's role is served, it is removed from the assembly with the endoscope. The sheath may be implemented as a single-use disposable item. The sheath may be removed from the assembly by removing the ureteroscope sheath combination and then taking the sheath off before reintroducing the ureteroscope. Alternatively, it may be removed by configuring the sheath to have a tear-strip or similar feature such that the sheath can be ripped off at the end of its use without having to withdraw the ureteroscope.

Persons skilled in the art will recognize that many modifications and variations are possible in the details, materials, and arrangements of the parts and actions which have been described and illustrated in order to explain the nature of the inventive subject matter and that such modifications and variations do not depart from the spirit and scope of the teachings and claims contained therein.

All patent and non-patent literature, if any, cited herein is hereby incorporated by references in its entirety for all purposes.

What is claimed is:

1. An illumination system for staged illumination in an endoscopic procedure, the system comprising:

an illumination apparatus that is configured for removable assembly with an endoscope, the illumination apparatus and endoscope being configured for insertion into a patient's body, the illumination apparatus and endoscope forming an illumination system for illuminating a target area in the patients body with sufficient illumination levels for an imaging system, at an insertion end of the endoscope, to receive reflected light and use the reflected light for required imaging;

wherein the illumination apparatus has a light source providing a first, relatively high level of illumination suitable for imaging a first, relatively large target area, either alone or in combination with a light source for the endoscope, and after removal of the illumination apparatus from the assembly, the light source for the endoscope provides only a second relatively lower level of illumination suitable for imaging a relatively small target area;

wherein the illumination apparatus further comprises a handle end and an opening near the handle end to fit the endoscope and hold the handle end of the illumination apparatus fixedly relative to the endoscope; and wherein the opening comprises a breakable body that breaches the opening when the breakable body is broken.

2. The illumination of system of claim 1 wherein the illumination apparatus has an outer diameter or peripheral dimensionality for use in a larger bodily passage, wherein the endoscope has an outer diameter or outer dimensionality for use in a relatively smaller bodily passageway after removal of the illumination apparatus.

3. The illumination system of claim 1 wherein the illumination apparatus comprises a tubular structure into which the endoscope is slideably disposable.

4. The illumination system of claim 3 wherein the tubular structure comprises a semi-rigid structure that is pushable but with sufficient flexibility to navigate bending passageways.

5. The illumination system of claim 4 wherein the illumination apparatus comprises a bladder access sheath configured for passage through a urethra and into a bladder and the endoscope comprises a ureteroscope configured for passage through a ureter to a kidney.

6. The illumination system of claim 1 wherein the illumination apparatus comprises a filament, filamentous, rod or rod-like structure that is slideably disposable within the outer diameter or outer dimensionality of the endoscope.

7. The illumination system of claim 6 wherein the illumination apparatus is configured for use within a predetermined existing channel of the endoscope.

8. The illumination system of claim 6 wherein the endoscope further comprises a working channel and the illumination apparatus is configured for use within the working channel and is configured so there is functional room for both the illumination apparatus and a guidewire at the same time.

9. The illumination system of claim 8 wherein the endoscope comprises a flexible ureteroscope and the illumination apparatus is at least about as flexible as the endoscope so as to not impede the use of the endoscope.

10. The illumination system of claim 1 wherein the illumination apparatus comprises an elongated element.

11. The illumination system of claim 10 wherein the elongated element has no other primary functionality in an endoscopic procedure other than supporting the light source of the illumination apparatus.

12. The illumination system of claim 10 wherein the elongated element has one or more other functionalities in an endoscopic procedure in addition to the functionality of supporting a light source of the illumination apparatus.

13. The illumination system of claim 12 wherein the other functionalities are serving as a bladder access sheath, a ureteral access sheath, a guide wire, a catheter, or a stent.

14. The illumination system of claim 1 wherein one of the illumination apparatus and the endoscope supports a light emitting device and the other is optically couplable to the light emitting device and has a light carrier that carries light from the light emitting device to the light source located at the insertion end of the endoscope or the light source located at an insertion end of the illumination apparatus for illuminating, a target area.

15. The illumination system of claim 14 wherein the endoscope supports the light emitting device and the illumination apparatus supports the light carriers.

16. The illumination system of claim 15 wherein the illumination apparatus comprises an access sheath for an endoscope.

17. The illumination system of claim 1 further comprising the endoscope.

18. The illumination system of claim 1 wherein the endoscope further comprises a Luer-type fitting and the opening to fit the endoscope fits by surrounding the Luer-type fitting.

19. The illumination system of claim 1 wherein the illumination apparatus comprises a body with a light carrier integrally molded therein optically coupled with light emissions devices to deliver light to the light source of the illumination apparatus.

20. An assembly for use in an endoscopic procedure comprising:
   an illumination apparatus having a light source and
   an endoscope having a light source,
   wherein the illumination apparatus and endoscope are removably assembled and arranged into an illumination system for inserting into and illuminating a target area in a patient's body with sufficient illumination levels for an imaging system at an insertion end of the endoscope to receive reflected light and use the reflected light for required imaging;
   wherein the light source of the illumination apparatus provides a first, relatively high level of illumination suitable for imaging a first, relatively large target area, either alone or in combination with the light source of the endoscope,
   wherein after removal of the illumination apparatus from the assembly, the light source of the endoscope provides only a second relatively lower level of illumination suitable for imaging a relatively small target area;
   wherein the illumination apparatus and the endoscope are arranged so that the light source of the illumination apparatus either alone or in combination with the light source of the endoscope illuminates a target site so that an imaging system of the endoscope receives the reflected light;
   wherein the illumination apparatus further comprises a handle end and an opening near the handle end to fit the endoscope and hold the handle end of the illumination apparatus fixedly relative to the endoscope; and
   wherein the opening comprises a breakable body that breaches the opening when the breakable body is broken.

21. The assembly of claim 20 wherein the illumination apparatus has an outer diameter or peripheral dimensionality for use in a larger bodily passage,
   wherein the endoscope has an outer diameter or outer dimensionality for use in a relatively smaller bodily passageway after removal of the illumination apparatus.

22. The assembly of claim 20 wherein the illumination apparatus comprises a tubular structure into which the endoscope is slideably disposed.

23. The assembly of claim 22 wherein the tubular structure comprises a semi-rigid structure that is pushable but with sufficient flexibility to navigate bending passageways.

24. The assembly of claim 23 wherein the illumination apparatus comprises a bladder access sheath configured for passage through a urethra and into a bladder and the endoscope comprises ureteroscope configured for passage through a ureter to a kidney.

25. The assembly of claim 20 wherein the illumination system comprises a filament, filamentous, rod, or rod-like structure that is slideably disposed within the outer diameter or outer dimensionality of the endoscope.

26. The assembly of claim 25 wherein the endoscope further comprises a predetermined existing channel and the illumination apparatus is configured for use within the predetermined existing channel of the endoscope.

27. The assembly of claim 25 wherein the endoscope further comprises a working channel and the illumination apparatus is configured for use within the working channel and configured so there is functional room for both the illumination apparatus and a guidewire at the same time.

28. The assembly of claim 27 wherein the endoscope comprises flexible ureteroscope end the illumination apparatus is at least about as flexible as the endoscope so as to not impede the use of the endoscope.

29. The assembly of claim 20 wherein the illumination apparatus comprises an elongated element.

30. The assembly of claim 29 wherein the elongated element has no other primary functionality in an endoscopic procedure other than supporting a light carrier.

31. The assembly of claim 29 wherein the elongated element has one or more other functionalities in an endoscopic procedure in addition to the functionality of supporting a light carrier.

32. The assembly of claim 31 wherein the other functionalities are sewing as a bladder access sheath, a ureteral access sheath, a guide wire, a catheter, or a stent.

33. The assembly of claim 20 wherein one of the illumination apparatus and the endoscope supports a light emitting device and the other is optically couplable to the light emitting device and has a light carrier that carries light from the light emitting device to the light source at the insertion end of the endoscope or an insertion end of the illumination apparatus for illuminating a target area.

34. The assembly of claim 33 wherein the endoscope supports the light emitting device and the illumination apparatus supports the light carriers.

35. The assembly of claim 34 wherein the illumination apparatus comprises an access sheath for an endoscope.

36. The assembly of claim 20
   wherein the endoscope further comprises one or more light emitting devices;
   wherein the illumination apparatus further comprises one or more light carriers having an insertion end and a handle end;
   wherein the handle end is optically coupled to the light emitting device; and
   wherein an insertion end of the illumination apparatus is the light source.

37. Previously prey n d) method of staged illumination in an endoscopic procedure comprising:
   introducing the illumination system of claim 1 into a body through a passageway;
   illuminating a first target site within the body using both the endoscope light source and the illumination apparatus light source;
   wherein the endoscope light source alone would not provide a sufficient amount light to illuminate the first target site; and
   wherein a second endoscope is not used.

38. The method of claim 37 wherein the body is a human body.

39. The method of claim 37 wherein the passageway is a urethra.

40. The method of claim 37 wherein illuminating the first target site is necessary to locate a passageway to a second target site.

41. The method of claim 40 wherein the second target site is a kidney and the method comprises the further step of removing the illumination apparatus and inserting the endoscope into a second passageway comprising a ureter.

42. The method of claim 41 further comprising advancing the endoscope up the ureter to the kidney and illuminating the kidney with the light source on the endoscope.

43. The method of claim 37 wherein the endoscope further comprises:
- one or more light emitting devices fixedly disposed on or in the endoscope;
- wherein the illumination apparatus further comprises one or more light carriers having an insertion end optically coupled to the one or more light emitting devices fixedly mounted on the endoscope handle; and
- wherein the illumination apparatus light source is the insertion end of the carriers.

* * * * *

UNITED STATES PATENT AND TRADEMARK OFFICE
CERTIFICATE OF CORRECTION

PATENT NO. : 8,512,232 B2
APPLICATION NO. : 12/555299
DATED : August 20, 2013
INVENTOR(S) : Rothberg et al.

Page 1 of 1

It is certified that error appears in the above-identified patent and that said Letters Patent is hereby corrected as shown below:

On Title page 2, col. 2, under item (56), Line 3, Reference Cited, Other Publications, Non-Patent Literature Documents; insert
--KODAK, "Shutter Operations for CCD and CMOS Image Sensors Revision 2.0" December 17, 2003 http://www.kodak.com/global/plugins/acrobat/en/business/ISS/supportdocs/S hutterOperations.pdf - 4 pages--

In the Claims:

Col. 9, Claim 1, Line 58 delete "patients" insert --patient's--
Col. 12, Claim 28, Line 11 delete "end" insert --and--
Col. 12, Claim 32, Line 24 delete "sewing" insert --serving--
Col. 12, Claim 37, Line 48 delete "Previously pre n d)" insert --A--

Signed and Sealed this
Eighth Day of October, 2013

Teresa Stanek Rea
*Deputy Director of the United States Patent and Trademark Office*